United States Patent [19]

Micetich et al.

[11] Patent Number: 4,562,073

[45] Date of Patent: * Dec. 31, 1985

[54] PENICILLIN DERIVATIVES

[75] Inventors: Ronald G. Micetich, Alberta, Canada; Shigeru Yamabe, Kobe, Japan; Motoaki Tanaka, Tokushima, Japan; Makoto Kajitani, Tokushima, Japan; Tomio Yamazaki, Tokushima, Japan; Naobumi Ishida, Tokushima, Japan

[73] Assignee: Taiho Pharmaceutical Company Limited, Tokyo, Japan

[*] Notice: The portion of the term of this patent subsequent to Jul. 16, 2002 has been disclaimed.

[21] Appl. No.: 519,491

[22] Filed: Aug. 1, 1983

[30] Foreign Application Priority Data

Dec. 24, 1982 [JP] Japan ................................ 57-233967
Feb. 10, 1983 [JP] Japan ................................ 58-21200

[51] Int. Cl.$^4$ .................. C07D 499/00; A61K 31/425
[52] U.S. Cl. ............................ 424/114; 260/245.2 R; 514/192
[58] Field of Search .............. 260/245.2 R, 245.2 T; 424/270, 271, 114; 514/192

[56] References Cited

U.S. PATENT DOCUMENTS 4,331,677 5/1982 Foglio et al. ................ 260/245.2 R Primary Examiner—Nicholas S. Rizzo Attorney, Agent, or Firm—Murray, Whisenhunt and Ferguson

[57] ABSTRACT

A penicillin derivative represented by the following formula

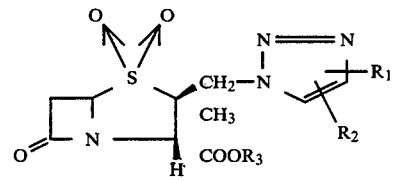

wherein $R_1$ is hydrogen or trialkylsilyl; $R_2$ is hydrogen, trialkylsilyl or $COOR_2'$ wherein $R_2'$ is hydrogen, $C_{1-18}$ alkyl, $C_{2-7}$ alkoxymethyl, $C_{3-8}$ alkylcarbonyloxymethyl, $C_{4-9}$ alkylcarbonyloxyethyl, $(C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl or group for forming a pharmaceutically acceptable salt; and $R_3$ has the same meaning as above $R_2'$.

18 Claims, No Drawings

PENICILLIN DERIVATIVES

This invention relates to penicillin derivatives and to a process for preparing them.

Of the commercially available antibiotics, β-lactam type antibiotics having a β-lactam ring, namely penicillins and cephalosporins, are best known and frequently used. Although widely used as useful chemotherapeutic drugs, the β-lactam type antibiotics can not achieve satisfactory effects against some types of microorganisms because of resistance of the microorganism to the β-lactam type antibiotics. The resistance thereof are usually attributable to β-lactamase produced by the microorganism. The β-lactamase is an enzyme which acts to cleave the β-lactam ring of the β-lactam type antibiotic, thereby causing the antibiotic to lose its antimicrobial activity. For this reason, the action of β-lactamase must be eliminated or inhibited so as to enable the β-lactam type antibiotic to produce satisfactory effects. The elimination or inhibition of the β-lactamase activity can be achieved by β-lactamase inhibitors, which are used conjointly with the β-lactam type antibiotic to increase the antimicrobial activity of the antibiotic.

It is an object of the present invention to provide novel compounds having β-lactamase inhibitory action.

It is another object of the invention to provide processes for preparing the same.

It is a further object of the invention to provide a pharmaceutical composition having excellent β-lactamase inhibitory action.

It is an additional object of the invention to provide compositions which, when combined with β-lactam type antibiotics, can increase the antibacterial activity of the antibiotics.

The penicillin derivatives of the present invention are represented by the formula

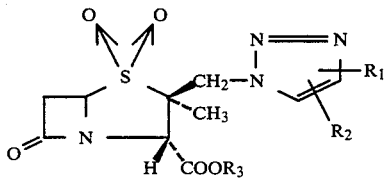

wherein $R_1$ is hydrogen or trialkylsilyl, $R_2$ is hydrogen, trialkylsilyl or $COOR_2'$ wherein $R_2'$ is hydrogen, $C_{1-18}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl and group for forming a pharmaceutically acceptable salt; and $R_3$ has the same meaning as $R_2'$.

The penicillin derivatives of the present invention are all novel compounds and have β-lactamase inhibitory properties, hence useful as β-lactamase inhibitory agents.

The penicillin derivatives of the invention, when used in combination with a known β-lactam type antibiotic, can increase the antimicrobial activity of the β-lactam type antibiotic.

Examples of antibiotics which can be used conjointly with the compounds of the present invention are β-lactam antibiotics which exhibit antibacterial action against gram-positive or gram-negative bacteria and which include commonly used penicillins such as ampicillin, amoxicillin, hetacillin, ciclacillin, mecillinam, carbenicillin, sulbenicillin, ticarcillin, piperacillin, apalcillin, methicillin, mezlocillin and salts thereof; esters of penicillins such as bacampicillin, carindacillin, talampicillin, carfecillin and pivmecillinam; cephalosporins such as cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cefadroxil, cephaloglycin, and salts thereof. The β-lactam antibiotics are usually used in an amount of about 0.1 to about 10 parts by weight, preferably about 0.2 to about 5 parts by weight, per part by weight of the compound of the invention.

Examples of the trialkylsilyl groups represented by $R_1$ and $R_2$ in the formula (I) include trialkylsilyl having straight-chain or branched-chain $C_{1-6}$ alkyl such as methyl, ethyl, propyl, isopropyl, butyl, tert-butyl, pentyl, hexyl, and the like.

Examples of the group $R_2'$ of $COOR_2'$ represented by $R_2$ in the formula (I) include; $C_{1-18}$ alkyl such as methyl, ethyl, propyl, isopropyl, tert-butyl, pentyl, hexyl, decyl, undecyl, dodecyl, tetradecyl, hexadecyl, octadecyl and like straight- or branched-chain alkyl; $C_{2-7}$ alkoxymethyl such as methoxymethyl, ethoxymethyl, propyloxymethyl, isopropyloxymethyl, butoxymethyl and hexyloxymethyl; $C_{3-8}$ alkylcarbonyloxymethyl such as methylcarbonyloxymethyl, ethylcarbonyloxymethyl, butylcarbonyloxymethyl and hexylcarbonyloxymethyl; $C_{4-9}$ alkylcarbonyloxyethyl such as methylcarbonyloxyethyl, ethylcarbonyloxyethyl, butylcarbonyloxyethyl and pivaloyloxyethyl; ($C_{5-7}$ cycloalkyl)carbonyloxymethyl such as cyclopentylcarbonyloxymethyl, cyclohexylcarbonyloxymethyl and cycloheptylcarbonyloxymethyl; $C_{9-14}$ benzylcarbonyloxyalkyl such as benzylcarbonyloxymethyl, benzylcarbonyloxyethyl, benzylcarbonyloxypropyl and benzylcarbonyloxybutyl; $C_{3-8}$ alkoxycarbonylmethyl such as methoxycarbonylmethyl, ethoxycarbonylmethyl, propyloxycarbonylmethyl and hexyloxycarbonylmethyl; $C_{4-9}$ alkoxycarbonylethyl such as methoxycarbonylethyl, ethoxycarbonylethyl, propyloxycarbonylethyl, butoxycarbonylethyl and hexyloxycarbonylethyl; halogenated $C_{1-6}$ alkyl substituted with 1 to 3 halogen atoms such as chloromethyl, 2,2-dibromoethyl and trichloroethyl; $C_{1-6}$ alkoxy- or nitro-substituted or unsubstituted benzyl such as p-methoxybenzyl, p-ethoxybenzyl, o-nitrobenzyl and p-nitrobenzyl; (5-substituted $C_{1-6}$ alkyl or phenyl or unsubstituted-2-oxo-1,3-dioxoden-4-yl)methyl such as (2-oxo-1,3-dioxoden-4-yl)methyl, (5-methyl-2-oxo-1,3-dioxoden-4-yl)methyl and (5-phenyl-2-oxo-1,3-dioxoden-4-yl)methyl; $C_{8-13}$ benzoyloxyalkyl such as benzoyloxymethyl, benzoyloxyethyl, benzoyloxypropyl and benzoyloxybutyl; etc.

Examples of the groups represented by $R_3$ in the formula (I) are the same as those exemplified in respect of the group $R_2'$.

The ester residues represented by $R_2'$ and $R_3$ include both carboxyl-protecting groups acceptable in the synthesis of penicillin compounds and pharmaceutically acceptable ester residues. A pharmaceutically acceptable ester having such residue is an ester which is easily hydrolyzed in vivo and which is a non-poisonous ester capable of rapidly decomposing in the blood or tissue of humans, thereby producing the corresponding acid of the formula (I) in which $R_3$ is hydrogen atom. Generally in the synthesis of penicillin compounds, ester-protecting groups are used in the art to protect penicillin carboxyl groups or other carboxyl groups. While it is difficult to determine which ester-protecting group should be used, consideration are usually given to select esters in which the protecting group per se is sufficiently stable in the reaction and which does not permit cleavage of the β-lactam ring in removal of the ester-protecting groups. Most commonly used as such ester-protecting groups are p-nitrobenzyl group, benzhydryl group, trichloroethyl group, trichlorosilyl group, tetrahydropyranyl group, etc. Examples of the pharmaceutically acceptable ester groups are phthalidyl, crotonolacton-4-yl, γ-butyrolacton-4-yl, (2-oxo-1,3-dioxoden-4-yl)methyl, etc.

Examples of the group for forming a pharmaceutically acceptable salt represented by $R_2'$ and $R_3$ in the formula (I) include; sodium, potassium, lithium, or like alkali metal atoms; calcium, magnesium or like alkaline earth metal atoms; cyclohexylamine, trimethylamine, diethanolamine or like organic amine; arginine, lysine or like basic amino acid residues; ammonium residues, etc.

The penicillin derivatives of the present invention having the formula (I) can be prepared by the processes as shown in reaction equations given below. The processes differ according to the kind of the groups represented by $R_1$ and $R_2$.

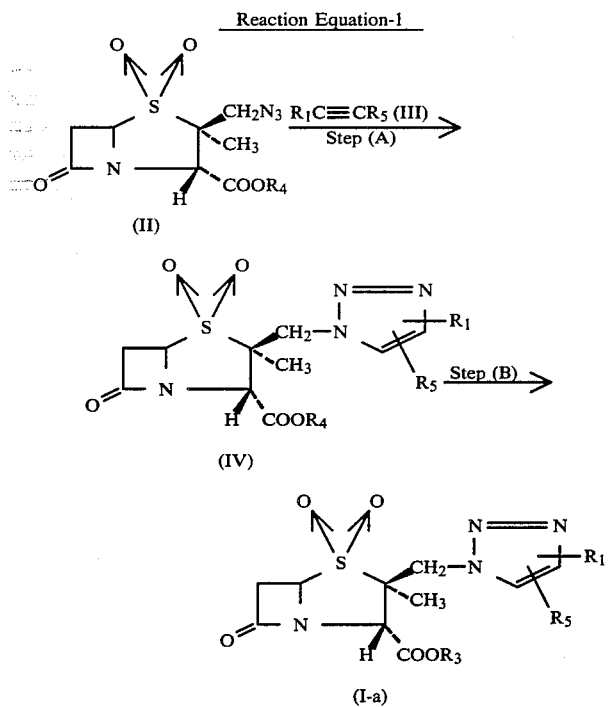

(I-a)

In the foregoing formulae, $R_1$ and $R_3$ are as defined above, $R_4$ is penicillin carboxyl-protecting group and $R_5$ is trialkylsilyl or $COOR_2'$ wherein $R_2'$ is as defined above.

Examples of the penicillin carboxyl protecting group expressed by $R_4$ include known groups such as those described in Japanese Unexamined Patent Publication No. 81380/1974 and H. E. Flynn, "Cephalosporins and Penicillins, Chemistry and Biology" (published in 1972 by Academic Press). Specific examples thereof are ethyl, propyl, tert-butyl, trichloroethyl and like substituted or unsubstituted alkyl groups; benzyl, diphenyl methyl, p-nitrobenzyl and like substituted or unsubstituted aralkyl groups; acetoxymethyl, acetoxyethyl, propionyloxyethyl, pivaloyloxyethyl, pivaloyloxypropyl, benzyloxymethyl, benzyloxyethyl, benzylcarbonyloxymethyl, cyclohexylcarbonyloxymethyl and like acyloxyalkyl groups, methoxymethyl, ethoxymethyl, benzyloxymethyl and like alkoxyalkyl groups; and other groups such as tetrahydropyranyl, dimethylaminoethyl, dimethylchlorosilyl, trichlorosilyl and like groups.

The steps (A) and (B) of the foregoing process will be described below in detail.

Step (A)

A penicillanic acid derivative of the formula (II) is reacted with an acetylene derivative of the formula (III) to provide a compound of the formula (IV). The reaction is conducted in a suitable solvent by reacting a known penicillanic acid derivative of the formula (II) with a known acetylene derivative of the formula (III) in an amount of about 1 to about 50 moles, preferably about 1 to about 10 moles, per mole of the derivative of the formula (II).

The solvents useful in the reaction are not particularly limited and include any of those which do not adversely affect the reaction. Specific examples of the solvents are an acetylene derivative of the formula (III) as used in excess amount or benzene, toluene, xylene and like aromatic hydrocarbons, tetrahydrofuran, dioxane or like ethers, acetone and like polar organic solvents; etc. These solvents are used singly or in mixture. The reaction proceeds usually at a temperature of between about 50° C. and a boiling point of the solvent, or at a temperature of less than 200° C. in a sealed reactor, and goes to completion in about 2 to about 72 hours.

Depending upon the kind of the penicillin carboxyl protecting group represented by $R_4$, the compounds of the formula (IV) obtained in step (A) may be esters of the penicillin derivatives of the present invention having the formula (I). The compounds of the formula (IV) are preferably subjected to de-esterification to form a derivative of the formula (I-a) in which $R_3$ is hydrogen which, in turn, is converted into a pharmaceutically acceptable salt or ester thereof as in the following step (B). The compound of the formula (IV) can also be made into an ester of the formula (I-a) by the conventional ester interchange reaction in the step (B).

Step (B)

The compound of the formula (IV) is subjected to de-esterification without or after isolation from the reaction mixture obtained in step (A), whereby a penicillin derivative of the formula (I-a) in which $R_3$ is hydrogen is obtained.

As the de-esterification method, reduction, hydrolysis, treatment with an acid and like method can be employed for converting the carboxyl-protecting group to carboxyl group. For example, if the carboxyl-protecting group is an active ester, the reaction frequently proceeds with ease under mild hydrolysis conditions or by merely bringing the ester into contact with water. The reduction method is employed when the carboxyl-protecting group is trichloroethylbenzyl, p-nitrobenzyl, diphenylmethyl or the like. Treatment with an acid is adopted when the carboxyl-protecting group is 4-methoxybenzyl, tert-butyl, trityl, diphenylmethyl, methoxymethyl, tetrahydropyranyl or the like.

The reduction can be conducted by treating the ester of the formula (IV) with a mixture of (a) zinc, zinc-amalgam or like metal and/or chromium chloride, chromium acetate or like chromium salt and (b) formic acid, acetic acid or like acid. Alternatively, the reduction can be conducted with use of a catalyst in hydrogen atomosphere in a solvent. Examples of the catalysts are platinum, platinum oxide, palladium, palladium oxide, palladium-barium sulfate, palladium-calcium carbonate, palladium-carbon, nickel oxide, Raney-nickel, etc. The solvents are not particularly limited so far as they do not adversely affect the reaction, and include methanol, ethanol and like alcohols; tetrahydrofuran, dioxane and like ethers; ethyl acetate and like esters; acetic acid and like fatty acids; and a mixture of these organic solvents and water.

The acids useful for eliminating the carboxyl-protecting group of the ester of the formula (I-a) are formic acid, acetic acid and like lower fatty acids; trichloroacetic acid, trifluoroacetic acid and like trihalogenated acetic acids; hydrochloric acid, hydrofluoric acid and like hydrohalogenic acids; p-toluene-sulfonic acid, trifluoromethane-sulfonic acid and like organic sulfonic acids; and a mixture of these. In this reaction, when the acid used is in a liquid state and acts also as a solvent, it is not necessary to use other solvents. However, dimethylformamide, dichloromethane, chloroform, tetrahydrofuran, acetone and like solvents which do not adversely affect the reaction may be used.

The penicillin derivative of the present invention having the formula (I-a) in which $R_3$ is hydrogen can be transformed by the salt-forming reaction or esterification commonly employed in the art into a pharmaceutically acceptable salt or ester as contemplated.

If the ester residue is, for example, 3-phthalidyl, crotonolacton-4-yl, γ-butyrolacton-4-yl or like group, the penicillin derivative of the formula (IV) can be alkylated by using 3-halogenated phthalide, 4-halogenated crotonolactone, 4-halogenated-γ-butyrolactone or the like. Suitable halogens of the foregoing halides include chlorine, bromine, iodine, etc. The reaction is carried out by dissolving the salt of the penicillin derivative of the formula (IV) in N,N-dimethylformamide or like suitable polar organic solvent and adding an approximately equimolecular amount of a halide to the solution. The reaction temperature ranges from about 0° to about 100° C., preferably from about 15° to about 35° C. Suitable salts of the penicillin derivative to be used in the esterification are salts of sodium, potassium or like alkali metals; salts of triethylamine, ethyldiisopropylamine, N-ethylpiperidine, N,N-dimethylaniline, N-methylmorpholine or like tertiary amines, etc. After completion of the reaction, the contemplated product can be easily separated by the conventional method and also can be purified, when required, by recrystallization, thin layer chromatography, column chromatography or like method.

The compound of the formula (II) to be used as the starting material in the step (A) is a novel compound undisclosed in literture and can be synthesized by the method described in Japanese Patent Application No. 69142/1982 (relating to an invention accomplished by us). The disclosed method comprises the steps of reacting a metal azide with a known derivative of penicillanic acid of the formula

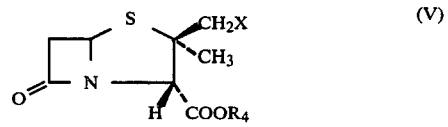

wherein X represents chlorine atom or bromine atom and $R_4$ is as defined above, oxydizing the reaction mixture and subjecting the resulting compound to de-esterification.

The foregoing method will be described below in detail. The reaction between the compound of the formula (V) and the metal azide is conducted in a suitable solvent by using the metal azide in an amount of about 1 to about 50 moles, preferably about 1 to about 10 moles, per mole of the compound of the formula (V). Examples of the metal azides which can be used include those commonly used, such as sodium azide, potassium azide and like azides of alkali metals, and barium azide and like azides of alkaline earth metals. Useful solvents are not particularly limited as far as they do not adversely affect the reaction. Examples of useful solvents are dimethylformamide, ethyl acetate, acetone, dichloromethane, tetrahydrofuran, dioxane, methanol, ethanol and like organic solvents. These organic solvents can be used singly or in mixtures. Also a mixture of such solvent and water is usable. The reaction proceeds at a temperature of usually about −20° to about 100° C., preferably about 0° to about 100° C. The resulting product can be used in subsequent oxidation without isolation, or alternatively after isolation and purification by a conventional method. The oxidation subsequent to the azide-forming reaction is conducted by using an oxidizing agent commonly employed such as permanganic acid, periodic acid, peracetic acid, performic acid, trifluoroperacetic acid, perbenzoic acid, m-chloroperbenzoic acid, hydrogen peroxide, etc. The oxidizing agent can be used in large excess, and may be employed preferably in an amount of about 1 to about 2 moles per mole of the starting compound. The oxidation is carried out usually in a suitable solvent. Useful solvents include any of those which do not adversely affect the oxidation reaction such as chloroform, pyridine, tetrahydrofuran, dioxane, methylene chloride, carbon tetrachloride, acetic acid, formic acid, dimethylformamide, water, etc. The oxidation is performed at a temperature which is not particularly limited but generally ranges from room temperature to cooling temperature, preferably about 0° to about 30° C.

The compound thus obtained is subjected to de-esterification whereby the compound of the formula (II) can be produced. The de-esterification is effected under the same conditions as shown in the reaction scheme of the step (B). The process for preparing the compound of the formula (II) is described in detail in reference examples to be set forth later.

Reaction Equation-2

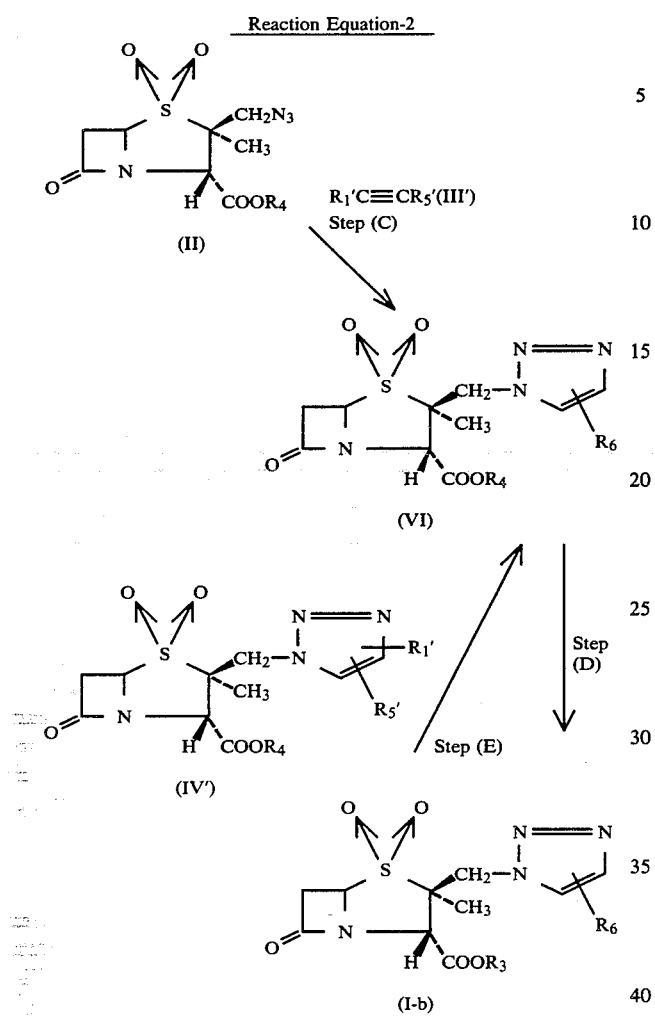

In the foregoing formulae, $R_4$ is as defined above, $R_1'$ and $R_5'$ are the same groups as those represented by $R_1$ and $R_5$ and at least one of them is trialkylsilyl group, and $R_6$ represents hydrogen or $COOR_2'$ wherein $R_2'$ is as defined above.

The compound of the formula (I) wherein at least one of $R_1$ and $R_2$ is hydrogen atom, namely the compound of the formula (I-b), can be prepared by the process shown above in Reaction Equation-2. The steps in the process are set forth below in detail.

Step (C)

The compound of the formula (II) is reacted with a compound of the formula (III') in a solvent such as dichloromethane, dichloroethane, chloroform or like halogenated hydrocarbons. During this reaction, reaction for removing the trialkylsilyl group proceeds at the same time, whereby a compound of the formula (VI) is produced. Useful solvents are not particularly limited as far as they are halogenated hydrocarbons. The reaction conditions including the reaction temperature, the proportions of the reagents to be used and the reaction time are similar to those in the step (A).

Depending upon the kind of the penicillin carboxyl-protecting group represented by $R_4$, the compound of the formula (VI) thus obtained may be the product as contemplated, i.e., an ester of the penicillin derivative of the formula (I). More preferably the ester of the formula (VI) is subjected to de-esterification as in the step (B) so that the compound is transformed to a penicillin derivative of the present invention during the formula (I-b) in which $R_3$ is hydrogen which is converted, when required, in the conventional manner into a pharmaceutically acceptable salt thereof or ester thereof as contemplated.

Step (D)

The compound of the formula (VI) is subjected to de-esterification after or without isolation from the reaction product obtained in the step (C), whereby a penicillin derivative of the formula (I-b) in which $R_3$ is hydrogen is produced. The de-esterification is carried out under the same conditions as those described above in respect of the step (B).

The compound of the formula (VI) can be prepared by the process in the step (C) and also by the process to be set forth below in step (E).

Step (E)

The compound of the formula (IV) obtained in the step (A) as shown in Reaction Equation-1 wherein at least one of $R_1$ and $R_5$ is trialkylsilyl, namely the compound of the formula (IV'), is subjected to reaction for removing the trialkylsilyl in the presence of potassium fluoride after or without isolation from the reaction product obtained in the step (A), whereby a compound of the formula (VI) is produced. The trialkylsilyl-removing reaction is conducted in a suitable solvent by using potassium fluoride in an amount of over about 1 mole, preferably about 1 mole, and a catalyst in an amount of about 1/50 to about 1/10 mole, both per mole of the compound of the formula (IV). Useful as the catalyst is a phase transfer catalyst such as quaternary ammonium salt, crown ether or the like. Examples of useful solvents are any suitable solvents which do not adversely affect the reaction and which include benzene, toluene, xylene or like aromatic hydrocarbons; acetonitrile, N,N-dimethylformamide, dimethylsulfoxide or like non-protonic polar solvents; etc. The reaction temperature and reaction time are appropriately determined. Generally the reaction is performed at a temperature in the range of room temperature to about 100° C., and completes in about 1 to about 10 hours.

Reaction Equation-3

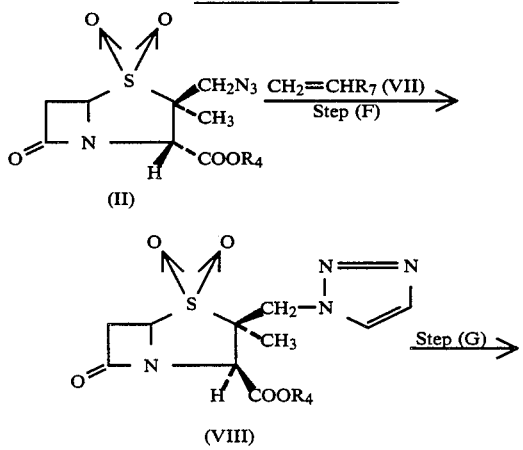

-continued
Reaction Equation-3

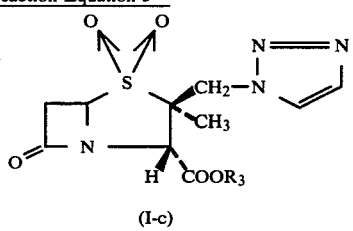

(I-c)

In the foregoing formulae, $R_4$ is as defined above, and $R_7$ represents acyloxy group.

Examples of the acyloxy groups represented by $R_7$ are lower acyloxy groups having 2 to 5 carbon atoms such as acetoxy, propionyloxy, butyryloxy, valeryloxy or like aliphatic acyloxy groups and benzoyloxy or like aromatic acyloxy groups, etc.

The compound of the formula (I) wherein $R_1$ and $R_2$ are hydrogen atoms, namely the compound of the formula (I-c), can be produced by the process as shown above in Reaction Equation-3.

The steps (F) and (G) in Reaction Equation-3 will be described below in detail.

Step (F)

The penicillanic acid derivative of the formula (II) is reacted with a vinyl derivative of the formula (VII) while reaction for removing the acyloxy group represented by $R_7$ in the formula (VII) is carried out, whereby a compound of the formula (VIII) is prepared. The reaction between the penicillanic acid derivative of the formula (II) and the vinyl derivative of the formula (VII) is conducted in the presence of or in the absence of a suitable solvent by using the vinyl derivative of the formula (VII) in an amount of at least about 1 mole, preferably from 1 to about 200 moles, per mole of the derivative of the formula (II), whereby there occurs simultaneously the acyloxy-removing reaction. The solvents which can be used are not particularly limited as far as they do not adversely affect the reaction. Specific examples thereof are benzene, toluene, xylene or like aromatic hydrocarbons, tetrahydrofuran, dioxane or like ethers, etc. The reaction is effected at a temperature ranging from about 50° C. to a boiling point of the solvent, or a temperature of less than 200° C. in a sealed reactor, and is completed in about 2 to about 72 hours. Depending on the kind of the penicillin carboxyl-protecting group represented by $R_4$ in the formula (VIII), the compound of the formula (VIII) thus obtained may be the product as contemplated, namely the ester of the penicillin derivative of the forumla (I). More preferably the compound of the formula (VIII) thus prepared is subjected to de-esterification as in the step (G) so that the compound is converted by the conventional method into a penicillin derivative of the formula (I-c) wherein $R_3$ is hydrogen which, in turn, is transformed by the conventional method into a pharmaceutically acceptable salt thereof or ester thereof as contemplated. The compound of the formula (VIII) can be made into a pharmaceutically acceptable salt thereof or ester thereof as contemplated by conducting an ester interchange or salt-forming reaction in the conventional manner.

Step (G)

The compound of the formula (VIII) is subjected to de-esterification after or without isolation from the reaction product obtained in the step (F), whereby a penicillin derivative of the formula (I-c) in which $R_3$ is hydrogen is produced. The reaction conditions for de-esterification are the same as those described in the step (B).

After completion of the reaction in each step, the contemplated compound producible in each step can be isolated from the reaction product or, when required, can be purified by the conventional method such as recrystallization method, thin-layer chromatography, column chromatography or the like.

The penicillin derivative of the present invention is mixed with the $\beta$-lactam type antibiotic substance to form a preparation which is orally or parenterally administered. Alternatively, the present compound and a suitable antibiotic can be separately administered. Thus the derivatives of the formula (I) can be used for treating infectious disease of human beings and other animals.

The composition of the present invention may be made into tablets, pills, capsules, granules, powders, syrups, lozenges, solutions, suspensions, etc. for oral administration and aqueous, suspending or water-soluble preparations for intravenous, subcutaneous or intramuscular injections.

Carriers useful in formulating the preparations are commonly used pharmaceutically acceptable non-toxic carriers such as gelatin, lactose, starch, magnesium stearate, talc, vegetable oil, animal oil, polyalkylene glycol, etc. The carrier may be used with other additives such as diluents, binders, buffer agents, preservatives, glazes, disintegrators, coating agents, etc.

The daily dose of the preparation can be appropriately determined and is not particularly limited. Preferably the daily dose is such that the total amount of the present compound and $\beta$-lactam antibiotic is about 1 to about 200 mg/Kg body weight for oral administration and about 1 to about 100 mg/Kg body weight for parenteral administration.

The present invention will be described below in more detail with reference to examples given below.

REFERENCE EXAMPLE 1

Preparation of benzhydryl 2$\beta$-azidiomethyl-2$\alpha$-methylpenam-3$\alpha$-carboxylate A solution of 5.00 g of sodium azide in 53 ml of water was added to a solution of benzhydryl 2$\beta$-chloromethyl-2$\alpha$-methylpenam-3$\alpha$-carboxylate (5.13 g) in dimethylformamide (155 ml). The mixture was stirred at room temperature for 4 hours. The resulting reaction mixture was poured into cooled water and the mixture was extracted with ethyl acetate. The ethyl acetate layer was washed with water, dried over magnesium sulfate and concentrated to provide 4.87 g of the contemplated product as oil in 93% yield.

Infrared absorption spectrum (nujol) $\nu$max (cm$^{-1}$): 2120, 1812, 1765

Nuclear magnetic resonance spectrum (CDCl$_3$) $\delta$ (ppm): 1.30 (3H, s), 3.25 (2H, m), 3.42 (1H, d), 3.63 (1H, d), 4.75 (1H, s), 4.76 (1H, m), 7.00 (1H, s), 7.40 (10H, s)

REFERENCE EXAMPLE 2

Preparation of benzhydryl 2β-azidomethyl-2α-methylpenam-3α-carboxylate 1,1-dioxide To a solution of benzhydryl 2β-azidomethyl-2α-methylpenam-3α-carboxylate (7.03 g) in a mixture of acetic acid (240 ml) and water (40 ml) was added potassium permanganate (6.02 g) over a period of more than 1 hour. The mixture was stirred at room temperature for 2.5 hours. The resulting reaction mixture was diluted with ice water. The precipitate was collected by filtration, and washed with water. The resulting product was dissolved in ethyl acetate and the solution was washed with an aqueous solution of sodium hydrogencarbonate and dried over magnesium sulfate. Concentration gave 5.48 g of the contemplated product in 72% yield.

Infrared absorption spectrum (nujol) νmax (cm$^{-1}$): 2120, 1812, 1765

Nuclear magnetic resonance spectrum (CDCl$_3$) δ (ppm): 1.18 (3H, s), 3.50 (2H, d), 3.72 (1H, d), 3.93 (1H, d), 4.60 (1H, m), 4.65 (1H, s), 7.00 (1H, s), 7.36 (10H, s)

REFERENCE EXAMPLE 3

Preparation of p-nitrobenzyl 2β-azidomethyl-2α-methylpenam-3α-carboxylate

The procedure of Reference Example 1 was repeated with the exception of using as the starting material p-nitrobenzyl 2β-chloromethyl-2α-methylpenam-3α-carboxylate, affording the above contemplated compound.

Infrared absorption spectrum (KBr) νmax (cm$^{-1}$): 2120, 1798. 1760

Nuclear magnetic resonance spectrum (CDCl$_3$) δ (ppm): 1.40 (3H, s), 3.12 (1H, dd), 3.50 (2H, s), 3.62 (1H, dd), 4.83 (1H, s), 5.29 (2H, s), 5.36 (1H, dd), 7.56 (2H, d), 8.26 (2H, d)

REFERENCE EXAMPLE 4

Preparation of p-nitrobenzyl 2β-azidomethyl-2α-methylpenam-3α-carboxylate-1,1-dioxide The procedure of Reference Example 2 was followed with the exception of using as the starting material p-nitrobenzyl 2β-azidomethyl-2α-methylpenam-3α-carboxylate, giving the above contemplated compound.

Infrared absorption spectrum (KBr) νmax (cm$^{-1}$): 2120, 1770

Nuclear magnetic resonance spectrum (CDCl$_3$) δ (ppm): 1.42 (3H, s), 3.45–3.60 (2H, m), 3.75 (1H, d), 3.96 (1H, d), 4.56–4.75 (1H, m), 4.64 (1H, s), 5.33 (2H, s), 7.56 (2H, d), 8.26 (2H, d)

EXAMPLE 1

Preparation of p-nitrobenzyl 2β-(4-ethoxycarbonyl-1,2,3-triazol-1-yl)methyl-2α-methylpenam-3α-carboxylate-1,1-dioxide (Compound 1) and p-nitrobenzyl 2β-(5-ethoxycarbonyl-1,2,3-triazol-1-yl)methyl-2α-methylpenam-3α-carboxylate-1,1-dioxide (Compound 2)

A 2.1 g quantity of p-nitrobenzyl 2β-azidomethyl-2α-methylpenam-3α-carboxylate-1,1-dioxide and 0.63 g of ethyl propiolate in 62 ml of benzene were refluxed with stirring under nitrogen atmosphere for 37 hours. The solvent was removed by distillation and the residue was subjected to column chromatography on silica gel to produce as a first eluted product 0.7 g of p-nitrobenzyl 2β-(5-ethoxycarbonyl-1,2,3-triazol-1-yl)methyl-2α-methylpenam-3α-carboxylate-1,1-dioxide in amorphous form (Compound 2) in 27% yield.

Infrared absorption spectrum (KBr) νmax (cm$^{-1}$): 1795, 1755, 1727

Nuclear magnetic resonance spectrum (CDCl$_3$) δ (ppm): 1.39 (3H, s), 1.39 (3H, t), 3.48–3.60 (2H, m), 4.39 (2H, q), 4.58–4.70 (1H, m), 5.11 (1H, s), 5.14 (1H, d), 5.25 (1H, d), 5.31 (1H, d), 5.56 (1H, d), 7.54 (2H, d), 8.09 (1H, s), 8.25 (2H, d).

There was obtained as a second eluted product 1.6 g of p-nitrobenzyl 2β-(4-ethoxycarbonyl-1,2,3-triazol-1-yl)methyl-2α-methylpenam-3α-carboxylate-1,1-dioxide in amorphous form (Compound 1) in 62% yield.

Infrared absorption spectrum (KBr) νmax (cm$^{-1}$): 1800, 1760 (sh), 1733

Nuclear magnetic resonance spectrum (CDCl$_3$) δ (ppm): 1.34 (3H, s), 1.41 (3H, t), 3.50–3.65 (2H, m), 4.42 (2H, q), 4.60–4.75 (2H, m), 5.09 (2H, s), 5.36 (2H, s), 7.59 (2H, d), 8.28 (2H, d), 8.30 (1H, s)

EXAMPLE 2

Preparation of p-nitrobenzyl 2β-(4-methoxycarbonyl-1,2,3-triazol-1-yl)methyl-2α-methylpenam-3α-carboxylate-1,1-dioxide (Compound 3) and p-nitrobenzyl 2β-(5-methoxycarbonyl-1,2,3-triazol-1-yl)methyl-2α-methylpenam-3α-carboxylate-1,1-dioxide (Compound 4)

The contemplated product was synthesized in the same manner as in Example 1 and eluted by column chromatography on silica gel. There was obtained as a first eluted product p-nitrobenzyl 2β-(5-methoxycarbonyl-1,2,3-triazol-1-yl)methyl-2α-methylpenam-3α-carboxylate-1,1-dioxide in amorphous form (Compound 4) in 26% yield.

Infrared absorption spectrum (KBr) νmax (cm$^{-1}$): 1795, 1727

Nuclear magnetic resonance spectrum (CDCl$_3$) δ (ppm): 1.39 (3H, s), 3.45–3.60 (2H, m), 3.94 (3H, s), 4.58–4.70 (1H, m), 5.09 (1H, s), 5.10–5.64 (4H, m), 7.54 (2H, d), 8.10 (1H, s), 8.25 (2H, d).

There was obtained as a second eluted product p-nitrobenzyl 2β-(4-methoxycarbonyl-1,2,3-triazol-1-yl)methyl-2α-methylpenam-3α-carboxylate-1,1-dioxide in amorphous form (Compound 3) in 61% yield.

Infrared absorption spectrum (KBr) νmax (cm$^{-1}$): 1798, 1730

Nuclear magnetic resonance spectrum (CDCl$_3$) δ (ppm): 1.33 (3H, s), 3.48–3.68 (2H, m), 3.96 (3H, s), 4.56–4.76 (2H, m) 5.09 (2H, s), 5.36 (2H, s), 7.60 (2H, d), 8.28 (2H, d), 8.30 (1H, s).

EXAMPLE 3

Preparation of benzhydryl 2β-(4-methoxycarbonyl-1,2,3-triazol-1-yl)methyl-2α-methylpenam-3α-carboxylate-1,1-dioxide (Compound 5) and benzhydryl 2β-(5-methoxycarbonyl-1,2,3-triazol-1-yl)methyl-2α-methylpenam-3α-carboxylate-1,1-dioxide (Compound 6)

The contemplated product was synthesized in the same manner as in Example 1 and eluted by column chromatography on silica gel. First there was eluted benzhydryl 2β-(5-methoxycarbonyl-1,2,3-triazol-1-yl)methyl-2α-methylpenam-3α-carboxylate-1,1-dioxide (Compound 6) in 18% yield.

Infrared absorption spectrum (KBr) νmax (cm⁻¹): 1800, 1727

Nuclear magnetic resonance spectrum (CDCl₃) δ (ppm): 1.20 (3H, s), 3.44–3.58 (2H, m), 3.91 (3H, s), 4.50–4.65 (1H, m), 5.24 (1H, d), 5.25 (1H, s), 5.45 (1H, d), 6.91 (1H, s), 7.20–7.40 (10H, m), 8.08 (1H, s).

Secondly there was eluted benzhydryl 2β-(4-methoxycarbonyl-1,2,3-triazol-1-yl)methyl-2α-methylpenam-3α-carboxylate-1,1-dioxide (compound 5) in 60% yield.

Infrared absorption spectrum (KBr) νmax (cm⁻¹): 1803, 1727

Nuclear magnetic resonance spectrum (CDCl₃) δ (ppm): 1.05 (3H, s), 3.48–3.62 (2H, m), 3.95 (3H, s), 4.55–4.75 (2H, m), 5.11 (2H, bs), 7.02 (1H, s), 7.20–7.50 (10H, m), 8.25 (1H, s).

EXAMPLE 4

Preparation of sodium 2β-(4-ethoxycarbonyl-1,2,3-triazol-1-yl)methyl-2α-methylpenam-3α-carboxylate-1,1-dioxide (Compound 7)

Hydrogenation was conducted at a low pressure and at room temperature by using 15 ml of ethyl acetate, 15 ml of water, 340 mg of p-nitrobenzyl 2β-(4-ethoxycarbonyl-1,2,3-triazol-1-yl)methyl-2α-methylpenam-3α-carboxylate-1,1-dioxide, 60 mg of 10% palladium charcoal and 110 mg of sodium hydrogencarbonate. After completion of absorption of hydrogen, the reaction mixture was filtered to separate the aqueous layer which was washed with benzene. The aqueous solution was concentrated at reduced pressure and the concentrate was subjected to column chromatography using an MCI gel, CHP-20 P (product of Mitsubishi Kasei Co., Ltd., Japan) to conduct gradient elution with a water-10% acetone water mixture. The eluate thus obtained was freeze-dried to afford 200 mg of the contemplated product (Compound 7) as white powder in 76% yield. The white powder decomposed at a temperature of more than 180° C.

Infrared absorption spectrum (KBr) νmax (cm⁻¹): 1782, 1720

Nuclear magnetic resonance spectrum (D₂O) δ (ppm): 1.39 (3H, t), 1.46 (3H, s), 3.45 (1H, dd), 3.72 (1H, dd), 4.44 (2H, q), 4.50 (1H, s), 4.96–5.10 (1H, m), 5.18 (1H, d), 5.42 (1H, d), 8.72 (1H, s)

EXAMPLE 5

Preparation of 2β-(4-ethoxycarbonyl-1,2,3-triazol-1-yl)methyl-2α-methylpenam-3α-carboxylic acid-1,1-dioxide (Compound 8)

Hydrogenation was conducted at room temperature and at a pressure of 3 atm. by using 4.2 g of p-nitrobenzyl 2β-(4-ethoxycarbonyl-1,2,3-triazol-1-yl)methyl-2α-methylpenam-3α-carboxylate-1,1-dioxide, 1.4 g of sodium hydrogencarbonate, 800 mg of 10% palladium charcoal, 100 ml of ethyl acetate and 100 ml of water. After completion of absorption of hydrogen, the reaction mixture was filtered and the aqueous layer was separated and washed with benzene. The pH of the aqueous layer was adjusted to 1 to 2 with hydrochloric acid. The aqueous layer was extracted with ethyl acetate and the extract was dried over magnesium sulfate. The solvent was distilled off and 3.0 g of the contemplated compound was produced in amorphous form in 97% yield.

Infrared absorption spectrum (KBr) νmax (cm⁻¹): 1798, 1726

Nuclear magnetic resonance spectrum (DMSO-d₆) δ (ppm): 1.31 (3H, t), 1.42 (3H, s), 3.31 (1H, dd), 3.73 (1H, dd), 4.32 (2H, q), 4.75–5.38 (4H, m), 8.76 (1H, s)

EXAMPLE 6

Preparation of chloromethyl 2β-(4-ethoxycarbonyl-1,2,3-triazol-1-yl)methyl-2α-methylpenam-3α-carboxylate-1,1-dioxide (Compound 9)

A 2.2 g quantity of sodium hydrogencarbonate and 0.2 g of tetrabutylammonium hydrogensulfate were added with stirring at a temperature of less than 10° C. to 2.4 g of 2β-(4-ethoxycarbonyl-1,2,3-triazol-1-yl)methyl-2α-methylpenam-3α-carboxylic acid-1,1-dioxide, 13.5 ml of dichloromethane and 13.5 ml of water. To the mixture was dropwise added at the same temperature 1.25 g of chloromethyl chlorosulfonate and the resulting mixture was stirred at room temperature for 30 minutes. The organic layer was separated, washed once with water and dried over magnesium sulfate. The solvent was removed by distillation and the residue was purified by column chromatography on silica gel, giving 2.2 g of the contemplated compound in amorphous form in 81% yield.

Infrared absorption spectrum (KBr) νmax (cm⁻¹): 1798, 1723

Nuclear magnetic resonance spectrum (CDCl₃) δ (ppm): 1.42 (3H, t), 1.48 (3H, s), 3.52–3.65 (2H, m), 4.36 (2H, q), 4.60–4.78 (2H, m), 5.10 (2H, s), 5.73 (1H, d), 5.90 (1H, d), 8.31 (1H, s)

EXAMPLE 7

Preparation of iodomethyl 2β-(4-ethoxycarbonyl-1,2,3-triazol-1-yl)methyl-2α-methylpenam-3α-carboxylate-1,1-dioxide (Compound 10)

A 1.73 g quantity of chloromethyl 2β-(4-ethoxycarbonyl-1,2,3-triazol-1-yl)methyl-2α-methylpenam-3α-carboxylic acid-1,1-dioxide and 1.3 g of sodium iodide were stirred in 3.4 ml of acetone at room temperature for 18 hours. To the reaction mixture was added 2.9 ml of water and the pH of the resulting mixture was adjusted to 7 to 8 with an aqueous solution of sodium hydrogencarbonate. After addition of 2.9 ml of water, the mixture was decolorized with an aqueous solution of 0.5M sodium thiosulfate, extracted with dichloromethane, washed with water and dried over magnesium sulfate. The solvent was removed by distillation and 1.9 g of the contemplated compound was prepared in amorphous form in 90% yeild.

Infrared absorption spectrum (KBr) νmax (cm⁻¹): 1798, 1725

Nuclear magnetic resonance spectrum (CDCl₃) δ (ppm): 1.43 (3H, t), 1.49 (3H, s), 3.52–3.68 (2H, m), 4.43 (2H, q), 4.59–4.78 (2H, m), 5.09 (2H, s), 5.96 (1H, d), 6.07 (1H, d), 8.32 (1H, s)

EXAMPLE 8

Preparation of sodium 2β-(5-ethoxycarbonyl-1,2,3-triazol-1-yl)methyl-2α-methylpenam-3α-carboxylate-1,1-dioxide (Compound 11)

A 220 mg of the contemplated compound was prepared in the form of white powder in the same manner as in Example 4 from 0.34 g of p-nitrobenzyl 2β-(5-ethoxycarbonyl-1,2,3-triazol-1-yl)methyl-2α-methylpenam-3α-carboxylate-1,1-dioxide in 83% yield.

The white powder thus obtained decomposed at a temperature of over 180° C.

Infrared absorption spectrum (KBr) νmax (cm⁻¹): 1788, 1736

Nuclear magnetic resonance spectrum (D$_2$O) δ (ppm): 1.39 (3H, t), 1.43 (3H, s), 3.40 (1H, dd), 3.71 (1H, dd), 4.46 (2H, q), 4.57 (1H, s), 4.96–5.05 (1H, m), 5.40 (1H, d), 5.82 (1H, d), 8.34 (1H, s)

EXAMPLE 9

Preparation of sodium 2β-(4-methoxycarbonyl-1,2,3-triazol-1-yl)methyl-2α-methylpenam-3α-carboxylate-1,1-dioxide (Compound 12)

A 0.18 g quantity of the contemplated product was prepared as white powder in the same manner as in Example 4 from 0.3 g of p-nitrobenzyl 2β-(4-methoxycarbonyl-1,2,3-triazol-1-yl)methyl-2α-methylpenam-3α-carboxylate-1,1-dioxide in 78% yield.

The white powder thus obtained decomposed at a temperature of over 184° C.

Infrared absorption spectrum (KBr) νmax (cm⁻¹): 1782, 1730

Nuclear magnetic resonance spectrum (D$_2$O) δ (ppm): 1.46 (3H, s), 3.45 (1H, dd), 3.73 (1H, dd), 3.97 (3H, s), 4.50 (1H, s), 4.81 (2H, s), 4.98–5.10 (1H, m), 5.18 (1H, d), 5.42 (1H, d), 8.72 (1H, s)

EXAMPLE 10

Preparation of sodium 2β-(5-methoxycarbonyl-1,2,3-triazol-1-yl)methyl-2α-methylpenam-3α-carboxylate-1,1-dioxide (Compound 13)

A 0.19 g quantity of the contemplated compound was prepared as white powder in the same manner as in Example 4 from 0.3 g of p-nitrobenzyl 2β-(5-methoxycarbonyl-1,2,3-triazol-1-yl)methyl-2α-methylpenam-3α-carboxylate-1,1-dioxide in 82% yield.

The white powder thus obtained decomposed at a temperature of over 180° C.

Infrared absorption spectrum (KBr) νmax (cm⁻¹): 1778, 1730

Nuclear magnetic resonance spectrum (D$_2$O) δ (ppm): 1.41 (3H, s), 3.41 (1H, dd), 3.71 (1H, dd), 3.98 (3H, s), 4.56 (1H, s), 4.95–5.08 (1H, m), 5.40 (1H, d), 5.83 (1H, d), 8.34 (1H, s)

EXAMPLE 11

Proparation of p-nitrobenzyl 2α-methyl-2β-[4-(p-nitrobenzyloxycarbonyl)-1,2,3-triazol-1-yl]methylpenam-3α-carboxylate-1,1-dioxide (Compound 14) and p-nitrobenzyl 2α-methyl-2β-[5-(p-nitrobenzyloxycarbonyl)-1,2,3-triazol-1-yl]methylpenam-3α-carboxylate-1,1-dioxide (Compound 15)

A 4 g quantity of p-nitrobenzyl 2β-adidomethyl-2α-methylpenam-3α-carboxylate-1,1-dioxide and 8.2 g of p-nitrobenzyl acetylene carboxylate in 100 ml of benzene were refluxed under nitrogen atmosphere for 12 hours. The solvent was distilled off at reduced pressure. The residue was subjected to column chromatography on silica gel to provide 3.6 g of p-nitrobenzyl 2α-methyl-2β-[4-(p-nitrobenzyloxycarbonyl)-1,2,3-triazol-1-yl]methylpenam-3α-carboxylate-1,1-dioxide (Compound 14) and 0.9 g of p-nitrobenzyl 2α-methyl-2β-[5-(p-nitrobenzyloxycarbonyl)-1,2,3-triazol-1-yl]methylpenam-3α-carboxylate-1,1-dioxide (Compound 15) both in amorphous form.

Compound 14

Infrared absorption spectrum (KBr) νmax (cm⁻¹): 1800, 1740

Nuclear magnetic resonance spectrum (CDCl$_3$) δ (ppm): 1.34 (3H, s), 3.3–3.8 (2H, m), 4.67 (1H, s), 4.60–4.76 (1H, m) 5.12 (2H, s), 5.37 (2H, s), 5.48 (2H, s), 7.5–7.7 (4H, m), 8.1–8.3 (4H, m), 8.37 (1H, s).

Compound 15

Infrared absorption spectrum (KBr) νmax (cm⁻¹): 1800, 1740

Nuclear magnetic resonance spectrum (CDCl$_3$) δ (ppm): 1.41 (3H, s), 3.3–3.7 (2H, m), 4.6–4.7 (1H, m), 5.07 (1H, s), 5.1–5.6 (4H, m), 5.46 (2H, s), 7.4–7.7 (4H, m), 8.15 (1H, s), 8.1–8.4 (4H, m)

EXAMPLE 12

Preparation of dipotassium 2β-(4-carboxy-1,2,3-triazol-1-yl)methyl-2α-methylpenam-3α-carboxylate-1,1-dioxide (Compound 16)

Hydrogenation was conducted in 100 ml of ethyl acetate and 100 ml of water at room temperature for 1 hour by using 3.6 g of p-nitrobenzyl 2α-methyl-2β-[4-(p-nitrobenzyloxycarbonyl)-1,2,3-triazol-1-yl]methylpenam-3α-carboxylate-1,1-dioxide, 2.0 g sodium hydrogencarbonate and 0.68 g of 10% palladium charcoal, catalyst. Thereafter the aqueous layer was separated and was washed once with ethyl acetate, and the pH thereof was adjusted to 1.5 to 1.7 with 6N hydrochloric acid. The aqueous solution was saturated with sodium chloride and extracted a few times with ethyl acetate. The ethyl acetate solutions thus formed were collected and dried over magnesium sulfate. The solvent was distilled off at reduced pressure to provide as the residue a foamed product of 2β-(4-carboxy-1,2,3-triazol-1-yl)methyl-2α-methylpenam-3α-carboxylic acid-1,1-dioxide.

A 2 g quantity of the 2β-(4-carboxy-1,2,3-triazol-1-yl)methyl-2α-methylpenam-3α-carboxylic acid-1,1-dioxide was dissolved in 20 ml of butanol. To the solution was added a solution of potassium 2-ethyl hexanoate in butanol, and the mixture was stirred awhile at room temperature. The precipitate was filtered to give 2.0 g of white solids having a melting point of over 178° C. (decomposition).

Infrared absorption spectrum (KBr) νmax (cm⁻¹): 1780, 1610

Nuclear magnetic resonance spectrum (D$_2$O) δ (ppm): 1.47 (3H, s), 3.49 (1H, dd), 3.77 (1H, dd), 4.53 (1H, s), 5.0–5.1 (1H, m), 5.16 (1H, d), 5.41 (1H, d), 8.47 (1H, s)

EXAMPLE 13

Preparation of dipotassium 2β-(5-carboxy-1,2,3-triazol-1-yl)methyl-2α-methylpenam-3α-carboxylate-1,1-dioxide (Compound 17)

White solid of the contemplated compound with a melting point of over 175° C. (decomposition) was prepared in the same manner as in Example 12 by using p-nitrobenzyl 2α-methyl-2β-[5-(p-nitrobenzyloxycarbonyl)-1,2,3-triazol-1-yl]methylpenam-3α-carboxylate-1,1-dioxide.

Infrared absorption spectrum (KBr) νmax (cm⁻¹): 1780, 1610

Nuclear magnetic resonance spectrum (D₂O) δ (ppm): 1.40 (3H, s), 3.43 (1H, dd), 3.71 (1H, dd), 4.58 (1H, s), 4.9–5.1 (1H, m), 5.36 (1H, d), 5.93 (1H, d), 8.04 (1H, s)

EXAMPLE 14

Preparation of benzhydryl 2β-(4-carboxy-1,2,3-triazol-1-yl)methyl-2α-methylpenam-3α-carboxylate-1,1-dioxide (Compound 18)

A 0.5 g quantity of benzhydryl 2β-azidomethyl-2α-methylpenam-3α-carboxylate-1,1-dioxide and 0.083 g of acetylenecarboxylic acid were stirred in 2 ml of dichloromethane at room temperature under nitrogen atmosphere for 24 hours. The solvent was removed by distillation at reduced pressure and to the residue oil was added benzene. The insolubles were filtered off and to the residue was added hexane to deposit crystals which were collected by filtration. Thus there was produced 0.23 g of white crystals which melt at 120° to 121° C.

Infrared absorption spectrum (KBr) νmax (cm⁻¹): 1805, 1745

Nuclear magnetic resonance spectrum (CDCl₃) δ (ppm): 1.07 (3H, s), 3.2–3.8 (2H, m), 4.5–4.7 (1H, m), 4.69 (1H, s), 5.12 (2H, bs), 7.02 (1H, s), 7.1–7.6 (10H, m), 8.33 (1H, s)

EXAMPLE 15

Preparation of disodium 2β-(4-carboxly-1,2,3-triazol-1-yl)methyl-2α-methylpenam-3α-carboxylate-1,1-dioxide (Compound 19)

Hydrogenation was conducted in 10 ml of ethyl acetate and 10 ml of water at room temperature for 30 minutes by using 49 mg of benzhydryl 2β-(4-carboxly-1,2,3-triazol-1-yl)methyl-2α-methylpenam-3α-carboxylate-1,1-dioxide, 15 ml of 10% palladium charcoal and 24 mg of sodium hydrogencarbonate. The aqueous layer was separated from the reaction mixture and washed with ethyl acetate, and was purified with an MCI gel, CHP-20P (product of Mitsubishi Kasei Co., Ltd., Japan). After freeze-drying, there was obtained a white amorphous product having a melting point of 220° to 250° C. (decomposition).

The values of the infrared absorption spectrum and nuclear magnetic resonance spectrum of the compound thus obtained were similar to those of Compound 16 prepared in Example 12.

EXAMPLE 16

Preparation of benzhydryl 2α-methyl-2β-(4-trimethylsilyl-1,2,3-triazol-1-yl)methylpenam-3α-carboxylate-1,1-dioxide (Compound 20)

A 150 mg quantity of benzhydryl 2β-azidomethyl-2α-methylpenam-3α-carboxylate-1,1-dioxide was reacted in a sealed reactor with 300 mg of trimethylsilylacetylene at 90° to 95° C. for 20 hours. The reaction mixture was concentrated at reduced pressure, giving 170 mg of white crystals which melt at 172° to 175° C.

Infrared absorption spectrum (KBr) νmax (cm⁻¹): 1805, 1755

Nuclear magnetic resonance spectrum (CDCl₃) δ (ppm): 0.32 (9H, s), 1.05 (3H, s), 3.3–3.7 (2H, m), 4.5–4.7 (1H, m), 4.65 (1H, s), 5.08 (2H, AB-q), 7.00 (1H, s), 7.3–7.5 (10H, m), 7.67 (1H, s)

EXAMPLE 17

Preparation of benzhydryl 2α-methyl-2β-(1,2,3-triazol-1-yl)methylpenam-3α-carboxylate-1,1-dioxide (Compound 21)

A 133 mg quantity of benzhydryl 2α-methyl-2β-(4-trimethylsilyl-1,2,3-triazol-1-yl)methylpenam-3α-carboxylate-1,1-dioxide, 3.26 g of 18-crown-6(1,4,7,10,13,16-hexaoxacyclooctadecane) and 15.8 mg of potassium fluoride were stirred in 0.7 ml of N,N-dimethylformamide at 50° to 60° C. for 5.5 hours. The reaction mixture was poured into excess iced water and the mixture was extracted a few times with ethyl acetate. The ethyl acetate extracts were collected and dried over magnesium sulfate. The solvent was distilled off at reduced pressure and the residue was purified by column chromatography on silica gel, whereby a white product was given which has a melting point of 206° to 208° C. (decomposition).

Infrared absorption spectrum (KBr) νmax (cm⁻¹): 1800, 1760

Nuclear magnetic resonance spectrum (CDCl₃) δ (ppm): 1.05 (3H, s), 3.3–3.7 (2H, m), 4.5–4.7 (1H, m), 4.65 (1H, s), 5.10 (2H, AB-q), 7.00 (1H, s), 7.3–7.5 (10H, m), 7.73 (1H, s)

EXAMPLE 18

Preparation of benzhydryl 2α-methyl-2β-(1,2,3-triazol-1-yl)methylpenam-3α-carboxylate-1,1-dioxide (Compound 21)

A 500 mg quantity of benzhydryl 2β-azidomethyl-2α-methylpenam-3α-carboxylate-1,1-dioxide, 335 mg of trimethylsilylacetylene and 2 ml of methylene chloride were reacted in a sealed reactor at 95° C. for 20 hours. The reaction mixture was concentrated at reduced pressure and the residue was purified by column chromatography on silica gel to provide white solids having a melting point of 203° to 204° C. (decomposition).

Fast atomic bombardment mass spectrum method: m/e=467(M+)

The values of the infrared absorption spectrum and nuclear magnetic resonance spectrum of te compound thus obtained were identical with those of Compound 21 obtained in Example 17.

EXAMPLE 19

Preparation of benzhydryl 2α-methyl-2β-(1,2,3-triazol-1-yl)methylpenam-3α-carboxylate-1,1-dioxide (Compound 21)

A 200 mg quantity of benzhydryl 2β-azidomethyl-2α-methylpenam-3α-carboxylate-1,1-dioxide was reacted with 10 ml of vinyl acetate in a sealed reactor at 100° to 110° C. for 30 hours. The reaction mixture was concentrated at reduced pressure. The residue was crystallized with cooled chloroform.

The white crystals thus obtained were found to have a melting point (decomposition) and the values of the nuclear magnetic resonance spectrum which were all identical with the values of Compound 21 obtained in Example 17.

EXAMPLE 20

Preparation of sodium
2α-methyl-2β-(1,2,3-triazol-1-yl)methylpenam-3α-carboxylate-1,1-dioxide (Compound 22)

Hydrogenation was conducted in 10 ml of ethyl acetate and 10 ml of water at room temperature for 30 minutes by using 45 mg of benzhydryl 2α-methyl-2β-(1,2,3-triazol-1-yl)methylpenam-3α-carboxylate-1,1-dioxide, 15 mg of 10% palladium charcoal and 16 mg of sodium hydrogencarbonate. The aqueous layer was separated from the reaction mixture and washed once with ethyl acetate. The aqueous solution was then purified with an MCI gel, CHP-20P (product of Mitsubishi Kasei Co., Ltd., Japan). After freeze-drying, there was obtained an amorphous product with a melting point of over 170° C. (decomposition).

Infrared absorption spectrum (KBr) $\nu$max (cm$^{-1}$): 1780, 1630

Nuclear magnetic resonance spectrum (D$_2$O) $\delta$ (ppm): 1.41 (3H, s), 3.45 (1H, dd), 3.72 (1H, dd), 4.48 (1H, s), 4.96–5.10 (1H, m), 5.25 (2H, AB-q), 7.85 (1H, d), 8.13 (1H, d)

EXAMPLE 21

Preparation of p-nitrobenzyl
2α-methyl-2β-(1,2,3-triazol-1-yl)methylpenam-3α-carboxylate-1,1-dioxide (Compound 23)

A 1.02 g quantity of p-nitrobenzyl 2β-azidomethyl-2α-methylpenam-3α-carboxylate-1,1-dioxide was reacted with 50 ml of vinyl acetate in a sealed reactor at 100° to 110° C. for 30 hours. The reaction mixture was concentrated at reduced pressure and the residue was purified by column chromatography on silica gel, giving 0.73 g of the contemplated compound in amorphous form in 67% yield which melts at 182° to 184° C.

Infrared absorption spectrum (KBr) $\nu$max (cm$^{-1}$): 1800, 1760

Nuclear magnetic resonance spectrum (CDCl$_3$) $\delta$ (ppm): 1.26 (3H, s), 3.5–3.6 (2, Hm), 4.66 (1H, s), 4.6–4.7 (1H, m) 5.07 (2H, s), 5.36 (2H, s), 7.61 (2H, d), 7.74 (1H, d), 7.80 (1H, d), 8.28 (2H, d)

EXAMPLE 22

Preparation of sodium
2α-methyl-2β-(4-trimethylsilyl-1,2,3-triazol-1-yl)methylpenam-3α-carboxylate-1,1-dioxide (Compound 24)

Hydrogenation was performed in 15 ml of ethyl acetate and 15 ml of water at room temperature for 30 minutes by using 200 mg of benzhydryl 2α-methyl-2β-(4-trimethylsilyl-1,2,3-triazol-1-yl)methylpenam-3α-carboxylate-1,1-dioxide, 50 mg of 10% palladium charcoal and 98 mg of sodium hydrogencarbonate. The aqueous layer was removed from the reaction mixture and washed once with ethyl acetate. The aqueous solution was purified with an MCI gel, CHP-20P (product of Mitsubishi Kasei Co., Ltd., Japan). After freeze-drying, there was obtained an amorphous product having a melting point of over 170° C. (decomposition).

Infrared absorption spectrum (KBr) $\nu$max (cm$^{-1}$): 1780, 1630

Nuclear magnetic resonance spectrum (D$_2$O) $\delta$ (ppm): 0.32 (9H, s), 1.38 (3H, s), 3.1–3.7 (2H, m), 4.46 (1H, s), 4.9–5.0 (1H, m), 5.23 (2H, AB-q), 8.16 (1H, s)

The compounds obtained in some of the examples were checked for β-lactamase inhibitory activity and antibacterial activity.

(1) Test for β-lactamase inhibitory activity

The inhibitory activity against penicillinase (β-lactamase) from Bacillus SP was measured by microiodometry Tanpakushitsu Kakusan Koso (Protein Nucleic Acid Enzyme), vol. 23, No. 5, pp 391–400 (1978) using a penicillin G as a substrate. Table 1 given below shows the results.

TABLE 1

| Compound | 50% Inhibitory Concentration |
|---|---|
| Compound 7 | 5.4 × 10$^{-8}$ M |
| Compound 11 | 3.4 × 10$^{-7}$ M |
| Compound 12 | 4.9 × 10$^{-8}$ M |
| Compound 13 | 3.0 × 10$^{-7}$ M |
| Compound 16 | 6.0 × 10$^{-7}$ M |
| Compound 17 | 1.7 × 10$^{-6}$ M |
| Compound 22 | 6.9 × 10$^{-7}$ M |
| Compound 24 | 5.1 × 10$^{-7}$ M |

(2) Test for antibacterial activity (1) Effects by ampicillin as combined with the present compound The compounds of the present invention and ampicillin, each singly used, were checked for minimal inhibitory concentration (MIC) against the bacteria listed in Table 2 given below by micro-broth dilution method ("American Journal Clinical Pathology" published in 1980, vol. 73, No. 3, pp 374 to 379). The MIC of ampicillin as combined with the present compound (10 μg/ml) was measured against the same bacteria. In the method, the bacteria cultivated in Mueller Hinton Broth (product of DIFCO) and diluted to 10$^7$ CFU/ml were inoculated into the same medium containing ampicillin and the present compound in a specific concentration, and incubated at 37° C. for 20 hours. Thereafter the growth of the microorganisms was observed to determine the minimal inhibitory concentration (MIC) for rendering the inoculated medium free from turbidity. The present compounds, singly used, turned out to be all more than 25 μg/ml in MIC. The bacteria as used in the test were those capable of producing β-lactamase, among which the bacteria marked * in the table are those collected from the living body of human hosts and the others are a stock culture.

In Table 2, the present compounds are shown by the compound number.

TABLE 2

| Test Bacteria | MIC (μg/ml) | | | | | | | | |
|---|---|---|---|---|---|---|---|---|---|
| | Ampicillin (singly used) | Present Compound (combined with ampicillin) | | | | | | | |
| | | 7 | 11 | 12 | 13 | 16 | 17 | 22 | 24 |
| S. aureus S-54 | 25 | 0.1 | 0.2 | 0.2 | 0.2 | 0.2 | 0.78 | 0.2 | 0.78 |
| S. aureus ATCC 90124 | 25 | 0.1 | 0.2 | 0.2 | 0.2 | 0.2 | 0.78 | 0.1 | 0.39 |
| E. coli TH-13* | 400 | 6.25 | 25 | 3.13 | 6.25 | 6.25 | 0.05 | 3.13 | 100 |
| E. coli TH-397* | 400 | 6.25 | 12.5 | 3.13 | 6.25 | 3.13 | 6.25 | 6.25 | 50 |

TABLE 2-continued

| Test Bacteria | Ampicillin (singly used) | MIC (μg/ml) Present Compound (combined with ampicillin) | | | | | | | |
|---|---|---|---|---|---|---|---|---|---|
| | | 7 | 11 | 12 | 13 | 16 | 17 | 22 | 24 |
| P. mirabilis 121 | 400 | 1.56 | 0.78 | 0.78 | 0.78 | 0.78 | 0.39 | 0.78 | 25 |
| P. vulgaris IID OX-19 | 100 | 0.78 | 0.78 | 0.39 | 0.39 | 1.56 | 1.56 | 0.78 | 1.56 |
| S. marcescens TH-05* | 400 | 12.5 | 25 | 12.5 | 25 | 6.25 | 1.56 | 3.13 | 100 |

(2) Effects by antibiotics as combined with the present compound

The compounds of the present invention, ampicillin, mecillinam, piperacillin and cephalexin, each singly used, were also tested for minimal inhibitory concentration against 30 strains of coliform bacilli collected from the living body of humans. The MIC of each antibiotic as combined with the present compound (10 μg/ml) was likewise measured. Table 3 to 6 indicate the results in which $MIC_{50}$ and $MIC_{70}$ indicate the minimal inhibitory concentration for inhibiting the growth of 50% and 70% respectively of the strains. The MICs of the present compounds singly used were all more than 25 μg/ml.

TABLE 3

| 30 Strains of coriform bacilli | Ampicillin singly used | Present compound as combined with ampicillin | | | | |
|---|---|---|---|---|---|---|
| | | Comp. 7 | Comp. 11 | Comp. 16 | Comp. 17 | Comp. 22 |
| $MIC_{50}$ (μg/ml) | 400 | 6.25 | 50 | 6.25 | 25 | 3.13 |
| $MIC_{70}$ (μg/ml) | 400 | 50 | 100 | 6.25 | 100 | 6.25 |

TABLE 4

| 30 Strains of coriform bacilli | Mecillinam singly used | Present compound as combined with mecillinam | | | | |
|---|---|---|---|---|---|---|
| | | Comp. 7 | Comp. 11 | Comp. 16 | Comp. 17 | Comp. 22 |
| $MIC_{50}$ (μg/ml) | 3.13 | 0.2 | 0.2 | 0.1 | 0.05 | 0.1 |
| $MIC_{70}$ (μg/ml) | 12.5 | 0.39 | 0.39 | 0.1 | 0.39 | 0.2 |

TABLE 5

| 30 Strains of coriform bacilli | Piperacillin singly used | Present compound as combined with piperacillin | | | | |
|---|---|---|---|---|---|---|
| | | Comp. 7 | Comp. 11 | Comp. 16 | Comp. 17 | Comp. 22 |
| $MIC_{50}$ (μg/ml) | 50 | 1.56 | 6.25 | 1.56 | 6.25 | 1.56 |
| $MIC_{70}$ (μg/ml) | 200 | 6.25 | 25 | 3.13 | 50 | 1.56 |

TABLE 6

| 30 Strains of coriform bacilli | Cephalexin singly used | Present compound as combined with cephalexin | | | | |
|---|---|---|---|---|---|---|
| | | Comp. 7 | Comp. 11 | Comp. 16 | Comp. 17 | Comp. 22 |
| $MIC_{50}$ (μg/ml) | 25 | 12.5 | 12.5 | 6.25 | 3.13 | 12.5 |
| $MIC_{70}$ (μg/ml) | 100 | 100 | 100 | 25 | 12.5 | 50 |

Given below are examples of preparation of the present antibacterial compositions.

| Preparation Example 1 | |
|---|---|
| Ampicillin | 200 mg |
| Compound 22 | 200 mg |
| Lactose | 100 mg |
| Crystalline cellulose | 57 mg |
| Magnesium stearate | 3 mg |
| Total | 560 mg |
| | (amount per capsule) |

The above ingredients are formulated in the proportions listed above into a capsule.

| Preparation Example 2 | |
|---|---|
| Amoxycillin | 100 mg |
| Compound 16 | 70 mg |
| Lactose | 330 mg |
| Corn starch | 490 mg |
| Hydroxypropyl methyl cellulose | 10 mg |
| Total | 1000 mg |
| | (amount per dose) |

The above ingredients are formulated in the proportions listed above into granules.

| Preparation Example 3 | |
|---|---|
| Pivmecillinam | 70 mg |
| Compound 17 | 70 mg |
| Lactose | 33 mg |
| Crystalline cellulose | 15 mg |
| Magnesium stearate | 3 mg |
| Talc | 4 mg |
| Corn starch | 15 mg |
| Hydroxypropyl methyl cellulose | 10 mg |
| Total | 220 mg |
| | (amount per tablet) |

The above ingredients are formulated in the proportions listed above into a tablet.

| Preparation Example 4 | |
|---|---|
| Compound 22 | 120 mg |
| Hydroxypropyl cellulose | 3 mg |
| Corn starch | 25 mg |
| Magnesium stearate | 2 mg |
| Total | 150 mg |
| | (amount per tablet) |

The above ingredients are formulated in the proportions listed above into a tablet.

We claim:

1. A penicillin derivative represented by the following formula

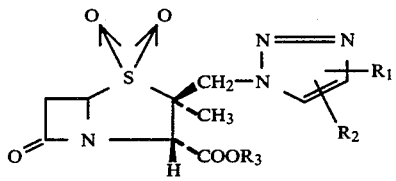

wherein $R_1$ is hydrogen or trialkylsily; $R_2$ is hydrogen, trialkylsilyl or $COOR_2'$ wherein $R_2'$ is hydrogen, $C_{1-18}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl or group for forming a pharmaceutically acceptable salt; and $R_3$ has the same meaning as above $R_2'$.

2. The penicillin derivative as defined in claim 1 wherein $R_3$ is $C_{2-7}$ alkoxymethyl.

3. The penicillin derivative as defined in claim 1 wherein $R_3$ is $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl or $C_{8-13}$ benzoyloxyalkyl.

4. The penicillin derivative as defined in claim 1 wherein $R_3$ is $C_{3-8}$ alkoxycarbonylmethyl or $C_{4-9}$ alkoxycarbonylethyl.

5. The penicillin derivative as defined in claim 1 wherein $R_3$ is phthalidyl.

6. The penicillin derivative as defined in claim 1 wherein $R_3$ is crotonolacton-4-yl and γ-butyrolacton-4-yl.

7. The penicillin derivative as defined in claim 1 wherein $R_3$ is (5-substituted $C_{1-6}$ alkyl or phenyl or unsubstituted-2-oxo-1,3-dioxoden-4-yl)methyl.

8. The penicillin derivative as defined in claim 1 wherein $R_3$ is a group for forming a pharmaceutically acceptable salt.

9. The penicillin derivative as defined in claim 1 wherein $R_3$ is $C_{1-6}$ alkyl or halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylchlorosilyl and trichlorosilyl.

10. The penicillin derivative as defined in claim 8 wherein the group for forming a pharmaceutically acceptable salt represented by $R_3$ is alkali metal atom, alkaline earth metal atom or ammonium, or the group $COOR_3$ represents a carboxylic acid salt formed from the carboxyl group and a member selected from the group consisting of cyclohexylamine, trimethylamine, diethanolamine, arginine and lysine.

11. The penicillin derivative as defined in claim 1 wherein $R_1$ and $R_2$ are hydrogen.

12. The penicillin derivative as defined in claim 1 wherein $R_1$ is hydrogen and $R_2$ is —$COOR_2'$.

13. The penicillin derivative as defined in claim 12 wherein $R_2'$ is $C_{1-18}$ alkyl.

14. The penicillin derivative as defined in claim 1 wherein $R_2$ is trialkylsilyl.

15. A pharmaceutical composition useful for treating bacterial infections in mammals, said composition comprising (A) a β-lactam antibiotic and (B) a compound of the formula

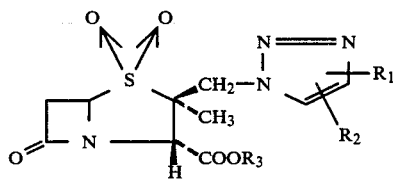

wherein $R_1$ is hydrogen or trialkylsilyl; $R_2$ is hydrogen, trialkylsilyl or $COOR_2'$ wherein $R_2'$ is hydrogen, $C_{1-18}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl or group for forming a pharmaceutically acceptable salt; and $R_3$ has the same meaning as above $R_2'$, the weight ratio of (A)/(B) being 0.1 to 10, said β-lactam antibiotics being selected from the group consisting of ampicillin, amoxicillin, hetacillin, ciclacillin, mecillinam, carbenicillin, sulbenicillin, ticarcillin, piperacillin, apalcillin, methicillin, mezlocillin, bacampicillin, carindacillin, talampicillin, carfecillin and pivmecillinam, cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cefadroxil and cephaloglycin; and pharmaceutically acceptable salts thereof.

16. A method of treating a bacterial infection in a mammal subject, said method comprising administering to said subject (A) a β-lactam antibiotic and (B) a compound of the formula

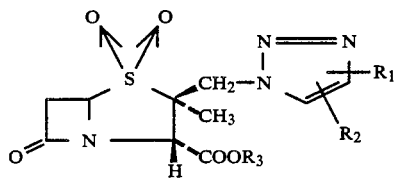

wherein $R_1$ is hydrogen or trialkylsilyl; $R_2$ is hydrogen, trialkylsilyl or $COOR_2'$ wherein $R_2'$ is hydrogen, $C_{1-18}$ alkyl, $C_{2-7}$ alkoxymethyl, $C_{3-8}$ alkylcarbonyloxymethyl, $C_{4-9}$ alkylcarbonyloxyethyl, ($C_{5-7}$ cycloalkyl)carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, halogenated $C_{1-6}$ alkyl substituted with 1 to 3 halogen atoms, $C_{1-6}$ alkoxy- or nitro-substituted or unsubstituted benzyl, benzhydryl, tetrahydropyranyl, dimethylaminoethyl, dimethylchlorosilyl, trichlorosilyl, (5-substituted $C_{1-6}$ alkyl or phenyl or unsubstituted-2-oxo-1,3-dioxoden-4-yl)methyl, $C_{8-13}$ benzoyloxyalkyl or group for forming a pharmaceutically acceptable salt; and $R_3$ has the same meaning as above $R_2'$, the weight ratio of (A)/(B) administered being 0.1 to 10, said β-lactam antibiotics being selected from the group consisting of ampicillin, amoxicillin, hetacillin, ciclacillin, mecillinam, carbenicillin, sulbenicillin, ticarcillin, piperacillin, apalcillin, methicillin, mezlocillin, bacampicillin, carindacillin, talampicillin, carfecillin and pivmecillinam, cephaloridine, cephalothin, cephapirin, cephacetrile, cefazolin, cephalexin, cefradine, cefotiam, cefamandole, cefuroxime, cefoxitin, cefmetazole, cefsulodin, cefoperazone, cefotaxime, ceftizoxime, cefmenoxime, latamoxef, cefaclor, cefroxadine, cefatrizine, cefadroxil and cephaloglycin; and pharmaceutically acceptable salts thereof.

17. The penicillin derivative as defined in claim 11 wherein $R_3$ is $C_{3-8}$ alkylcarbonyloxymethyl, hydrogen, $C_{4-9}$ alkylcarbonyloxyethyl, ($C_{5-7}$ cycloalkyl)-carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, (5-substituted $C_{1-6}$ alkyl or phenyl or unsubstituted-2-oxo-1,3-dioxoden-4-yl)methyl, $C_{8-13}$ benzoyloxyalkyl or group for forming a pharmaceutically acceptable salt.

18. The penicillin derivative as defined in claim 12 wherein $R_3$ is $C_{3-8}$ alkylcarbonyloxymethyl, hydrogen, $C_{4-9}$ alkylcarbonyloxyethyl, ($C_{5-7}$ cycloalkyl)-carbonyloxymethyl, $C_{9-14}$ benzylcarbonyloxyalkyl, $C_{3-8}$ alkoxycarbonylmethyl, $C_{4-9}$ alkoxycarbonylethyl, phthalidyl, crotonolacton-4-yl, γ-butyrolacton-4-yl, (5-substituted $C_{1-6}$ alkyl or phenyl or unsubstituted-2-oxo-1,3-dioxoden-4-yl)methyl, $C_{8-13}$ benzoyloxyalkyl or group for forming a pharmaceutically acceptable salt.

* * * * *

UNITED STATES PATENT AND TRADEMARK OFFICE

CERTIFICATE EXTENDING PATENT TERM
UNDER 35 U.S.C. § 156

PATENT NO.     : 4,562,073

DATED          : December 31, 1985

INVENTOR(S)    : Ronald G. Micetich et al.

PATENT OWNER   : Taiho Pharmaceutical Company

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

1,344 DAYS from the original expiration date of the patent, June 6, 2003, subject to the requirements of 35 U.S.C. § 41, with all rights pertaining thereto as provided by 35 U.S.C. § 156(b).

I have caused the seal of the Patent and Trademark Office to be affixed this 25th day of April 1996.

Bruce A. Lehman
Assistant Secretary of Commerce and
  Commissioner of Patents and Trademarks